United States Patent [19]

Parris

[11] Patent Number: 4,646,743

[45] Date of Patent: Mar. 3, 1987

[54] THERAPY RADIATION APPARATUS FOR VETERINARY MEDICINE

[76] Inventor: Danny M. Parris, P.O. Box 429, Inola, Okla. 74036

[21] Appl. No.: 608,395

[22] Filed: May 9, 1984

[51] Int. Cl.⁴ .............................................. A61N 5/06
[52] U.S. Cl. .................... 128/396; 128/398
[58] Field of Search ............... 128/395, 396, 397, 398, 128/303.1

[56] References Cited

U.S. PATENT DOCUMENTS

| | | | |
|---|---|---|---|
| 1,771,076 | 7/1930 | Chesney | 128/396 |
| 3,014,156 | 12/1961 | Osterhammel | 128/395 X |
| 3,516,411 | 6/1970 | Adler | 128/399 X |
| 3,785,383 | 1/1974 | Dotto | 128/395 |
| 4,232,678 | 11/1980 | Skovajsa | 128/395 |
| 4,553,546 | 11/1985 | Javelle . | |

FOREIGN PATENT DOCUMENTS 2371935  7/1978  France .................. 128/395

Primary Examiner—Anton O. Oechsle

[57] ABSTRACT

An apparatus for treating animal bodies with radiation of a selected frequency or wave length for providing therapy in the tissues and bones of the animal. It makes use of a modulated radiation from an infrared source which may be broadband radiation in a selected range of wave lengths. The radiation may be from a single or from multiple small sources in a selected array, mounted in suitable apparatus in suitable flexible means for wrapping it around the outer surface of an animal, or in the form of a rigid probe for irradiating internal surfaces of the body.

6 Claims, 4 Drawing Figures

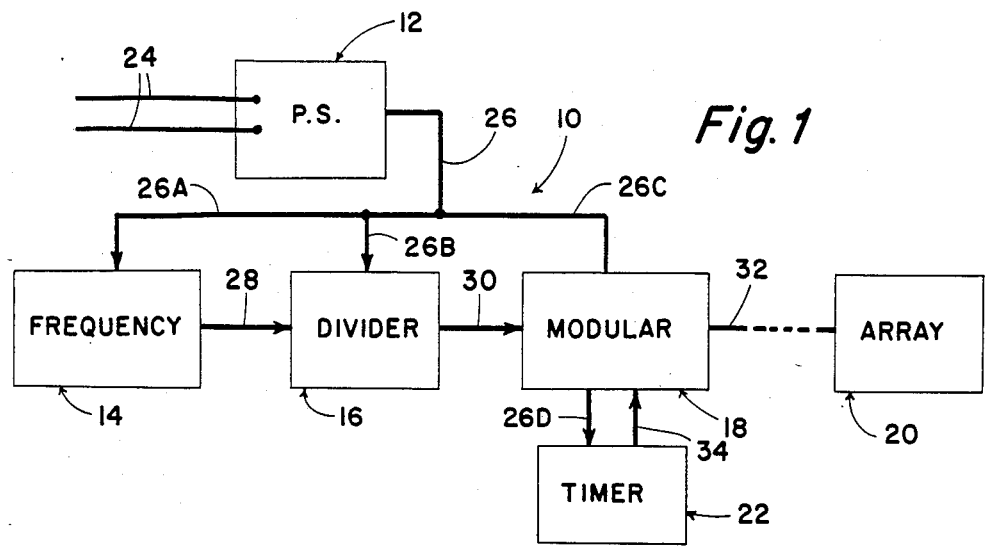
Fig. 1
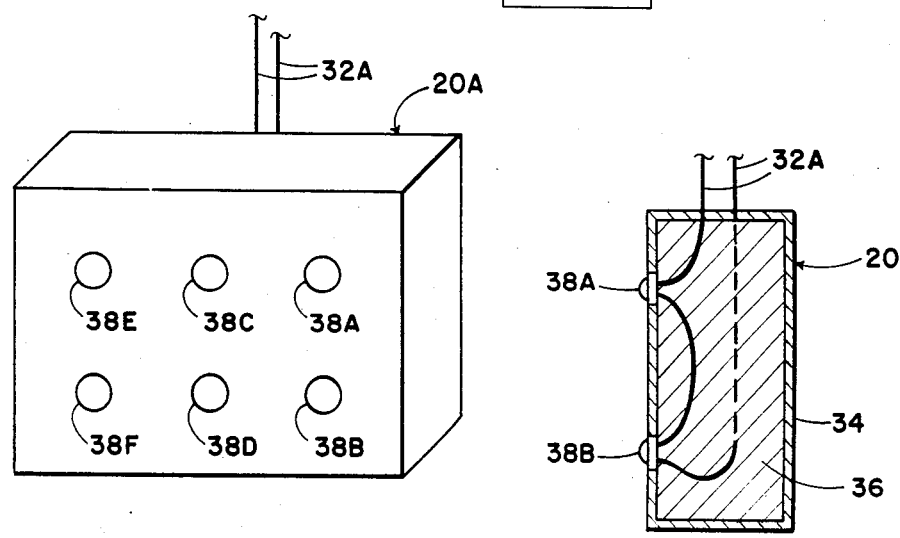
Fig. 2
Fig. 3
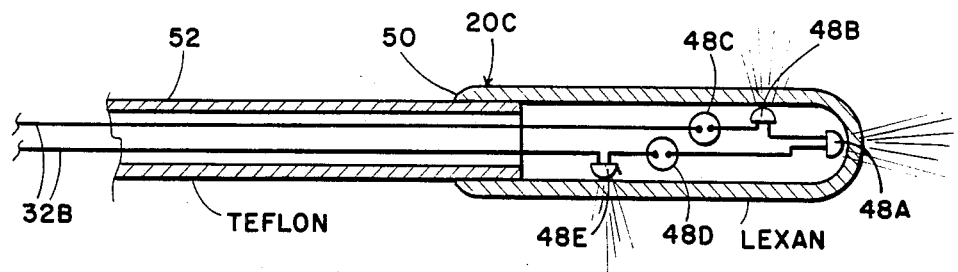
Fig. 4

THERAPY RADIATION APPARATUS FOR VETERINARY MEDICINE

BACKGROUND OF THE INVENTION

1. Field of the Invention

This invention lies in the field of application of radiation therapy, where the specific radiation is in the infrared region.

Still more particularly, this invention is devoted to the treatment of tissues under the surface of the outer skin, or on the surfaces of bones below the outer skin, and the surfaces of inner cavities in the body.

2. Description of the Prior Art

There have been a number of devices publicized in the literature and in the patent literature, relative to the use of low frequency electromagnetic radiation on a human body. More recently, research has been done on the application of radiation therapy in the infrared region for use in treating animals, more particularly, horses. It has been learned that the infrared region of the spectrum is more useful than other ranges of the spectrum of electromagnetic radiation.

SUMMARY OF THE INVENTION

It is a primary object of this invention to provide a device for irradiating the body of live animals by means of solid state devices, which will produce radiation in the infrared region of the spectrum. The radiation may be a collimated single frequency radiation, or relatively broad band uncollimated radiation.

The only explanation of how this radiation can work is that if the selected frequency of the radiation matches the natural nuclear resonance in the cells of the tissue, or bone, then the energy will be absorbed in the tissue and will promote faster growth and healthier tissues.

These and other objects are realized and the limitations of the prior art are overcome in this invention by providing an apparatus which will provide selected voltages for supplying the radiation sources and for precisely modulating the current at a high frequency selected for the particular situation in the tissues of the body. Different periods or frequencies of modulation are used to stimulate specific cell functions of body tissue.

The power for irradiating the tissues is delivered to a blanket or rod of selected design in order to accommodate placing a plurality of diodes in contact with the outer surface of the animal or at a selected distance away from the outside surface and to apply a voltage which will provide a selected total energy of radiation dependent on the kind of therapy that is required.

With an array of infrared diodes, they are inserted into openings in a flexible sheet of neoprene and held in there by elastic forces. This sheet is backed up by a rubber like foam. This provides a certain amount of contact pressure between the sheet and the body surface, so that the sheet will fit itself to the contour of the surface. The entire blanket is then covered in neoprene for the purpose of handling, etc. The blanket is attached to the body surface by means of adhesive strips or bandages.

Means are provided for varying the frequency of modulation of radiation and also for timing the irradiation into longer on and off periods.

BRIEF DESCRIPTION OF THE DRAWINGS

These and other objects and advantages of this invention and a better understanding of the principles and details of the invention will be evident from the following description taken in conjunction with the appended drawings, in which:

FIG. 1 represents a schematic circuit diagram for generating the power and frequencies of modulation and timing of the apparatus.

FIGS. 2 and 3 show two views of one embodiment of the apparatus for holding the irradiating diodes into proper relation with the animal body.

FIG. 4 illustrates a type of rigid probe which can be inserted into various cavities in the body of the animal.

DESCRIPTION OF THE PREFERRED EMBODIMENT

Before explaining in detail the present invention, it is to be understood that the invention is not limited in its application to details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Referring now to FIG. 1 there is shown one embodiment of this invention, indicated in general by the numeral 10. A power supply is provided with electrical power from batteries over leads 24. Suitable regulated voltages as required, are provided on the output lead 26 of the power supply 12. The leads 26 serve over leads 26A a high frequency oscillator 14, the output of which goes on a lead 28 to a frequency divider 16. The divider has an input of power over line 26B and an output of signal over line 30 to the modulator 18 which is also supplied by power from over lead 26C. The power output of the divider is an alternating voltage of selected multiple frequencies.

There is a timer 22 which is supplied by power over line 26D and outputs a switching signal on line 34 to the modulator 18. The output of the modulator on line 32 goes to the radiation device which may be a single broadband infrared diode, for example, or it may be an array of broadband infrared diodes.

FIGS. 2 and 3 show one embodiment of the radiation array by means of which the radiation output of one or more diodes is directed to the selected outer surface of the animal's body. The array device indicated in general by numeral 20A. In end view cross section, it comprises a flexible pad or blanket, in one surface of which, openings are provided for seating one diode in each of the openings, such as, for example, 38A, 38B, 38C, 38D and so on. These diodes are facing outward and the surface facing out of the drawing is, of course, the surface applied to the body.

The construction is made of a pad of rubber foam of rectangular shape and suitable thickness which is covered by a sheet of neoprene of sufficient thickness to hold the diodes in place in holes cut through the sheet. The cord 32A represents the cord 32 of FIG. 1 which carries two conductors supplying the voltage in series across the six, or more, or less, diodes shown. The entire foam blanket and the neoprene sheet are covered by additional flexible protective material so it can be used and handled quite roughly without being damaged.

The cross sectional view in FIG. 3 illustrates the presence of the outer covering 34, and the compliant rubber foam 36 with the diodes 38A and 38B inserted into the openings cut into the surface of the front neoprene covering.

This type of blanket would normally be held in contact with the outer skin of the animal by means of adhesive tape. For legs, for example, it can be held by means of bandages wrapped around the leg and the blanket.

Referring now to FIG. 4 there is shown a type of rigid probe for holding one or more of the diodes in the wall of a tube of plastic indicated by the numeral 50. There are a plurality of holes drilled through this closed tube and the diodes are inserted from the inside into the openings. They are connected electricallly in series, between the two conductors 32B, which are connected to the output of the modulator, lead 32. The interior of the probe can be filled with suitable foam setting material, that could be poured in and by proper temperature or chemical control, caused to foam and hold the diodes in their proper opening.

Any particular selected array can, of course, be used. The one shown in FIG. 4 involves one diode in the end, and a helical placement of the diodes in one revolution of the tube 50 of the probe. A smaller diameter tube 52 which may be made of Teflon, for example, is inserted into one end of the larger tube holding the diodes 48A, 48B, 48C, 48D and 48E, for example. This plastic tube has been made of Lexan. Both plastic materials are well known in the art.

Of course, the diodes in FIG. 4 can be powered by the modulated and timed signals on line 32 just as they are modulated and timed in the blanket of FIGS. 2 and 3.

In experiments carried out with this apparatus, it was found that for certain types of therapy, certain magnitudes of voltage and power output of the diodes is required for beneficial effect. Also, several types of lasers have been investigated such as a helium neon laser which has a radiation wave length of 632 nanometers. There are also diode lasers having gallium arsenade diodes which operate at a radiation wave length of 904 nanometers. It appears that some wave length between these 632 and 904 nanometers, is closer to the optimum frequency of the cells of the body tissue and thus the broadband infrared diode which operates rather broad band, centered at about 880 nanometers, is found extremely useful. Also, the non-laser diodes have more to offer in one respect and that is that they provide an expanding beam of radiation rather than a collimated narrow beam. Thus, the infrared diode provides a more uniform radiation per square centimeter of an exposed surface.

While I speak of particular flexible or rigid materials such as neoprene, Lexan, Teflon, etc., other suitable materials can be used, as is well known in the art.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. A radiation device for use in veterinary medicine, for treating exterior and interior portions of animal bodies, comprising:
   (a) power supply means providing selected voltages;
   (b) high frequency oscillator means;
   (c) frequency divider means responsive to said oscillator means, and adapted to control switch means for modulating a voltage supply for at least one non-laser broad band infrared radiation diode providing an expanding beam of radiation; and
   (d) means for applying said at least one non-laser broad band infrared radiation diode to a dermal surface of an animal.

2. The apparatus as in claim 1 and including timer means to control the total time of application of said radiation.

3. The apparatus as in claim 1 and including means to apply any one of a plurality of modulation frequencies to said at least one non-laser broad band infrared radiation diode.

4. The apparatus as in claim 1 and including means for applying an array of non laser broad band infrared diodes to the dermal surface of an animal.

5. The apparatus as in claim 4 in which said dermal surface is the outer surface of the body of said animal.

6. The apparatus as in claim 4 in which said dermal surface is the surface of an interior body cavity.

* * * * *